(12) United States Patent
Cole

(10) Patent No.: US 8,202,279 B2
(45) Date of Patent: Jun. 19, 2012

(54) FOLLICULAR EXTRACTION PUNCH AND METHOD

(76) Inventor: John P. Cole, Atlanta, GA (US)

( * ) Notice: Subject to any disclaimer, the term of this patent is extended or adjusted under 35 U.S.C. 154(b) by 323 days.

(21) Appl. No.: 11/558,338

(22) Filed: Nov. 9, 2006

(65) Prior Publication Data

US 2007/0149985 A1 Jun. 28, 2007

Related U.S. Application Data

(63) Continuation-in-part of application No. 10/795,835, filed on Mar. 9, 2004, now Pat. No. 7,172,604.

(51) Int. Cl.
*A61B 17/50* (2006.01)
(52) U.S. Cl. .......................................... 606/133
(58) Field of Classification Search .................. 606/133, 606/131, 107, 187, 184
See application file for complete search history.

(56) References Cited

U.S. PATENT DOCUMENTS

| | | | |
|---|---|---|---|
| 2,360,051 A | 10/1944 | Eweson | |
| 3,035,580 A | 5/1962 | Methodi | |
| 3,913,566 A * | 10/1975 | Lacey | 600/567 |
| 3,990,453 A | 11/1976 | Douvas et al. | |
| 3,998,230 A | 12/1976 | Miller | |
| 4,263,913 A | 4/1981 | Malmin | |
| 4,476,864 A | 10/1984 | Tezel | |
| 4,479,445 A | 10/1984 | Walker | |
| 4,798,213 A | 1/1989 | Doppelt | |
| 4,873,991 A | 10/1989 | Skinner | |
| 4,994,028 A | 2/1991 | Leonard et al. | |
| 5,269,316 A | 12/1993 | Spitainy | |
| 5,417,683 A | 5/1995 | Shiao | |
| 5,423,330 A | 6/1995 | Lee | |
| 5,439,475 A | 8/1995 | Bennett | |
| 5,507,765 A | 4/1996 | Mott | |
| 5,578,054 A | 11/1996 | Arnold | |
| 5,613,978 A | 3/1997 | Harding | |
| 5,662,661 A | 9/1997 | Boudjema | |
| 5,676,680 A | 10/1997 | Lim | |
| 5,693,064 A | 12/1997 | Arnold | |
| 5,707,362 A | 1/1998 | Yoon | |
| 5,725,553 A | 3/1998 | Moenning | |
| 5,766,177 A | 6/1998 | Lucas-Dean | |
| 5,792,163 A | 8/1998 | Hitzig | |

(Continued)

FOREIGN PATENT DOCUMENTS

FR 2744624 8/1997

(Continued)

OTHER PUBLICATIONS

Unger et al., "Hair Transplantation", Fourth Edition, Revised and Expanded, pp. 353-354, Jan. 1, 2004.

(Continued)

*Primary Examiner* — Ryan Severson
*Assistant Examiner* — Sarah Simpson
(74) *Attorney, Agent, or Firm* — Berkeley Law & Technology Group, LLP

(57) ABSTRACT

A method and apparatus disclosed herein may incise into a patient's skin to a precise depth and at a specific angle with respect to a surface of the patient's to extract individual follicular groups or individual follicular units. An apparatus as disclosed herein may precisely limit a depth of an incision, and perform a circular incision around a hair, follicular unit, or follicular cluster without damaging any hair shafts.

24 Claims, 5 Drawing Sheets

U.S. PATENT DOCUMENTS

| | | | |
|---|---|---|---|
| 5,792,169 | A | 8/1998 | Markman |
| 5,817,120 | A | 10/1998 | Rassman |
| 5,827,297 | A | 10/1998 | Boudjema |
| 5,895,403 | A | 4/1999 | Collinsworth |
| 5,922,000 | A | 7/1999 | Chodorow |
| 5,989,273 | A | 11/1999 | Arnold |
| 6,059,807 | A | 5/2000 | Boudjema |
| 6,120,521 | A | 9/2000 | Casparian |
| 6,315,737 | B1 | 11/2001 | Skinner |
| 6,461,369 | B1 | 10/2002 | Kim |
| 6,482,178 | B1 | 11/2002 | Andrews et al. |
| 6,572,625 | B1 * | 6/2003 | Rassman ............... 606/133 |
| 6,579,281 | B2 | 6/2003 | Palmer et al. |
| 6,601,748 | B1 | 8/2003 | Fung |
| 6,641,564 | B1 | 11/2003 | Kraus |
| 6,861,250 | B1 | 3/2005 | Cole |
| 7,172,604 | B2 | 2/2007 | Cole |
| 7,261,721 | B2 * | 8/2007 | Feller ............... 606/133 |
| 2002/0013572 | A1 | 1/2002 | Berlin |
| 2002/0099393 | A1 | 7/2002 | Fleischman et al. |
| 2003/0040766 | A1 | 2/2003 | Werner |
| 2003/0097143 | A1 | 5/2003 | Mittelstaedt |
| 2003/0097144 | A1 * | 5/2003 | Lee ............... 606/187 |
| 2003/0120297 | A1 | 6/2003 | Beyerlein |
| 2003/0233112 | A1 | 12/2003 | Alden et al. |
| 2003/0233114 | A1 | 12/2003 | Merboth et al. |
| 2004/0193203 | A1 | 9/2004 | Pak et al. |
| 2004/0199195 | A1 | 10/2004 | Dumontelle |
| 2004/0260241 | A1 | 12/2004 | Yamamoto et al. |
| 2005/0075651 | A1 * | 4/2005 | Ortiz ............... 606/131 |
| 2005/0187573 | A1 | 8/2005 | Rassman et al. |
| 2005/0203545 | A1 | 9/2005 | Cole |
| 2005/0267506 | A1 | 12/2005 | Harris |
| 2006/0072805 | A1 | 4/2006 | Tsipouras et al. |
| 2006/0273135 | A1 | 12/2006 | Beetel |
| 2010/0125287 | A1 | 5/2010 | Cole et al. |

FOREIGN PATENT DOCUMENTS

| | | |
|---|---|---|
| FR | 2744624 A | 8/1997 |
| FR | 2744624 A | 8/1997 |
| WO | 98/47434 | 10/1998 |
| WO | 0110307 | 2/2001 |
| WO | 03/096906 | 11/2003 |
| WO | 03/096906 A | 11/2003 |

OTHER PUBLICATIONS

Brandy, "New Instrumentation for Hair Transplatation Surgery", Dermatologic Surgery, Elsevier Science, New York, NY, vol. 24, No. 6, pp. 629-631, Jun. 1998.

Non-Final Office action mailed Apr. 19, 2005 in related matter U.S. Appl. No. 10/795,835, 4 pages.

Amendment filed May 18, 2005 in related matter U.S. Appl. No. 10/795,835, 10 pages.

Non-final Office action mailed Jul. 12, 2005 in related matter U.S. Appl. No. 10/795,835, 9 pages.

Amendment filed Oct. 12, 2005 in related matter U.S. Appl. No. 10/795,835, 4 pages.

Non-final Office action mailed Jan. 4, 2006 in related matter U.S. Appl. No. 10/795,835, 7 pages.

Amendment filed May 2, 2006 in related matter U.S. Appl. No. 10/795,835, 11 pages.

Notice of Allowance mailed Aug. 1, 2006 in related U.S. Appl. No. 10/795,835, 6 pages.

Issue Fee and Formal Drawings filed Nov. 1, 2006 in related matter U.S. Appl. No. 10/795,835, 8 pages.

Issue Notification mailed Jan. 17, 2007 in related matter U.S. Appl. No. 10/795,835, 1 page.

Certificate of Correction filed Jun. 19, 2007 in related U.S. Appl. No. 10/795,835, 2 pages.

Certificate of Correction mailed Jul. 31, 2007 in related matter U.S. Appl. No. 10/795,835, 1 page.

European Search Report, in related matter PCT/US2004/023533, Dated Mar. 27, 2007, 81 pages.

Preliminary Amendment filed Aug. 17, 2006 in related matter U.S. Appl. No. 10/506,564, 7 pages.

Second Preliminary Amendment filed Nov. 9, 2006 in related matter U.S. Appl. No. 11/506,564, 13 pages.

Preliminary Amendment filed Nov. 30, 2006 in related matter U.S. Appl. No. 11/565,553, 18 pages.

Patent Application filed Jan. 3, 2006 in related matter U.S. Appl. No. 11/325,388, 46 pages.

Preliminary Amendment filed Jun. 4, 2007 in related matter U.S. Appl. No. 11/508,669, 4 pages.

Patent Application filed Oct. 16, 2006 in related matter U.S. Appl. No. 11/549,942, 29 pages.

International Search Report and Written Opinion mailed Jul. 24, 2008, in related matter No. PCT/US07/81519, 133 pages.

Bernstein Medical Center for Hair Restoration, "Instrumentation for Three-Step FUE" 3 pages, www.bernsteinmedical.com/hair-transplant/follicular-extraction-Instrumentation.php Jan. 2006.

Office action: Restriction Requirement mailed Apr. 1, 2009 in related matter U.S. Appl. No. 11/549,942, 8 pages.

Office action: Restriction Requirement mailed Jun. 3, 2009 in related U.S. Appl. No. 11/549,942, 8 pages.

Response to Restriction Requirement filed Jul. 2, 2009 in related U.S. Appl. No. 11/549,942, 11 pages.

Office action: mailed Sep. 16, 2009 in U.S. Appl. No. 11/549,942, 19 pages.

Office Action Restriction Requirement mailed Dec. 8, 2009 in U.S. Appl. No. 11/506,564, 7 pages.

Response filed Feb. 28, 2010 in U.S. Appl. No. 11/565,553, 10 pages.

Office Action mailed Apr. 23, 2010 in U.S. Appl. No. 11/506,564, 20 pages.

Office Action Restriction Requirement mailed Dec. 7, 2009 in U.S. Appl. No. 11/565,553, 7 pages.

Response filed Feb. 8, 2010 in U.S. Appl. No. 11/565,553, 18 pages.

Office Action mailed May 12, 2010 in U.S. Appl. No. 11/565,556, 25 pages.

Office Action Restriction Requirement mailed Dec. 8, 2009 in U.S. Appl. No. 11/325,388, 7 pages.

Response filed Feb. 8, 2010 in U.S. Appl. No. 11/325,388, 13 pages.

Office Action mailed Apr. 27, 2010 in U.S. Appl. No. 11/325,388, 30 pages.

Office Action restriction Requirement mailed Dec. 8, 2009 in U.S. Appl. No. 11/508,669, 8 pages.

Response filed Feb. 8, 2010 in U.S. Appl. No. 11/508,669, 20 pages.

Office Action mailed Apr. 28, 2010 in U.S. Appl. No. 11/508,669, 19 pages.

Filing Documents for entering the European stage for EP Application No. 04778857.5, Oct. 9, 2006, 7 pages.

Notification of EP Publication No. for EP Application No. 04778857.5, Nov. 15, 2006 1 page.

Supplementatry EP Search Report for Application No. 04778857.5, Mar. 27, 2007, 5 pages.

Official Letter from EPO for Application No. 04778857.5, Jul. 27, 2007, 1 page.

Official Communication for Application No. 04778857.5, Feb. 20, 2008, 8 pages.

Notification Concerning Availability of the Publication of the International Application for Application No. PCT/US2009/064424, May 20, 2010, 2 pages.

Notification Concerning Submission or Transmittal of Priority Document for Application No. PCT/US 2009/064424, Dec. 3, 2009, 1 page.

Notification of Receipt of Record Copy for Application No. PCT/US 2009/064424, Dec. 2, 2009, 1 page.

Application for PCT/US 2009/064424, Nov. 13, 2009, 72 pages.

Publication of International Search Report for Application No. PCT/US2007/060056, Aug. 2, 2007, 2 pages.

Written Opinion for Application No. PCT/US2007/060056, Jul. 16, 2008, 9 pages.

Notification Concerning Transmittal of International Preliminary Report on Patentability for Application No. PCT/US2007/060056, Sep. 25, 2008, 2 pages.

Entry into EP Phase for Application No. PCT/US2007/060056, Jun. 6, 2008, 3 pages.

Notification Concerning Submission or Transmittal of Priority Document for Application No. PCT/US2007/060056, Jun. 14, 2007, 1 page.
Application for PCT/US2007/060056, Jan. 3, 2007, 68 pages.
International Search Report for Application No. PCT/US2004/023533, Sep. 13, 2005, 1 page.
Decision on Terminal Disclaimer, mailed Sep. 19, 2010 for U.S. Appl. No. 11/506,564, 1 page.
Final Office Action, mailed Nov. 29, 2010 for U.S. Appl. No. 11/506,564, 15 pages.
Examiner's interview summary, mailed Feb. 24, 2011 for U.S. Appl. No. 11/506,564, 4 pages.
Request for continued examination and terminal disclaimer, mailed Mar. 29, 2011 for U.S. Appl. No. 11/506,564, 33 pages.
Non-Final Office Action, mailed May 23, 2011 for U.S. Appl. No. 11/506,564, 21 pages.
Final Office Action, mailed Nov. 5, 2010 for U.S. Appl. No. 11/565,553, 21 pages.
Interview Summary, mailed Jan. 10, 2011 for U.S. Appl. No. 11/565,553, 4 pages.
Request for continued examination, mailed May 5, 2011 for U.S. Appl. No. 11/565,553, 37 pages.
Final Rejection, mailed Nov. 24, 2010 for U.S. Appl. No. 11/325,388, 26 pages.
Interview summary, mailed Feb. 23, 2011 for U.S. Appl. No. 11/325,388, 5 pages.
Request for continued examination and terminal disclaimer, mailed Mar. 24, 2011 for U.S. Appl. No. 11/325,388, 34 pages.
Non-Final Office Action, mailed May 9, 2011 for U.S. Appl. No. 11/325,388, 21 pages.
Decision on Terminal Disclaimer, mailed May 19, 2011 for U.S. Appl. No. 11/325,388, 1 page.
Interview summary, mailed Jan. 3, 2011 for U.S. Appl. No. 11/508,669, 4 pages.
Request for continued examination and terminal disclaimer, mailed Jan. 26, 2011 for U.S. Appl. No. 11/508,669, 41 pages.
Decision on Terminal Disclaimer, mailed Apr. 15, 2011 for U.S. Appl. No. 11/508,669, 3 pages.
Boudjema, "The FUExtractor® System: New Instrumentation to Improve Follicular Unit Extraction", Hair Transplantation Forum International, 1 page, Sep./Oct. 2006.
Bernstein Medical Center for Hair Restoration, "Instrumentation for Three-Step FUE" 3 pages, www.bernsteinmedical.com/hair-transplant/follicular-extraction-Instrumentation.php, Jan. 2006.
Unger, et al., "Hair Transplantation", Fourth Edition, Revised and Expanded, pp. 353-354, Jan. 1, 2004.
Brandy, "New Instrumentation for Hair Transplantation Surgery", Dermatologic Surgery, Elsevier Science, New York, NY, vol. 24, No. 6, pp. 629-631, Jun. 1998.
Application as filed (U.S. Appl. No. 10/795,835, filed Mar. 9, 2004), 56 pages.
Notice to file missing parts mailed May 25, 2004 for U.S. Appl. No. 10/795,835, 2 pages.
Response to notice to file missing parts mailed Jun. 17, 2004 for U.S. Appl. No. 10/795,835, 2 pages.
Restriction Requirement mailed Apr. 19, 2005 for U.S. Appl. No. 10/795,835, 4 pages.
Response to Restriction Requirement mailed May 18, 2005 for U.S. Appl. No. 10/795,835, 11 pages.
Office Action mailed Jul. 12, 2005 for U.S. Appl. No. 10/795,835, 9 pages.
Office Action Response mailed Oct. 12, 2005 for U.S. Appl. No. 10/795,835, 5 pages.
Office Action mailed Jan. 4, 2006 for U.S. Appl. No. 10/795,835, 7 pages.
Office Action Response mailed May 2, 2006 for U.S. Appl. No. 10/795,835, 12 pages.
Notice of Allowance mailed Aug. 1, 2006 for U.S. Appl. No. 10/795,835, 8 pages.
Issue Fee Payment, Corrected Drawings and Comments on Statement of Reasons for Allowance mailed Nov. 1, 2006 for U.S. Appl. No. 10/795,835, 9 pages.
Request for Certificate of Correction mailed Jun. 19, 2007 for U.S. Appl. No. 10/795,835, 5 pages.
Certificate of Correction mailed Jul. 31, 2007 for U.S. Appl. No. 10/795,835, 1 page.
Application as filed (U.S. Appl. No. 11/506,564, filed Aug. 17, 2006), 64 pages.
Notice to file missing parts mailed Sep. 5, 2006 for U.S. Appl. No. 11/506,564, 2 pages.
Response to notice to file missing parts mailed Nov. 1, 2006 for U.S. Appl. No. 11/506,564, 14 pages.
Second Preliminary Amendment mailed Nov. 9, 2006 for U.S. Appl. No. 11/506,564, 14 pages.
Filing Receipt mailed Nov. 9, 2006 for U.S. Appl. No. 11/506,564, 3 pages.
Rescission of Non-Publication request mailed Aug. 27, 2008 for U.S. Appl. No. 11/506,564, 1 page.
Petition to Revive Application mailed Aug. 27, 2008 for U.S. Appl. No. 11/506,564, 8 pages.
Communication regarding Rescission of Non-Publication Request mailed Nov. 20, 2007 for U.S. Appl. No. 11/506,564, 4 pages.
Notice of Publication mailed Nov. 23, 2007 for U.S. Appl. No. 11/506,564, 2 pages.
Restriction Requirement mailed Dec. 8, 2009 for U.S. Appl. No. 11/506,564, 7 pages.
Response to Restriction Requirement mailed Feb. 8, 2010 for U.S. Appl. No. 11/506,564, 2 pages.
Office Action mailed Apr. 23, 2010 for U.S. Appl. No. 11/506,564, 12 pages.
Interview Summary mailed Aug. 4, 2010 for U.S. Appl. No. 11/506,564, 2 pages.
Office Action Response and Terminal Disclaimer mailed Aug. 23, 2010 for U.S. Appl. No. 11/506,564, 19 pages.
Application as filed (U.S. Appl. No. 11/565,553, filed Nov. 30, 2006), 60 pages.
Notice to file missing parts mailed Sep. 5, 2006 for U.S. Appl. No. 11/565,553, 2 pages.
Filing Receipt mailed Jan. 16, 2007 for U.S. Appl. No. 11/565,553, 3 pages.
Response to notice to file missing parts mailed Jun. 1, 2007 for U.S. Appl. No. 11/565,553, 4 pages.
Updated Filing Receipt mailed Jun. 6, 2007 for U.S. Appl. No. 11/565,553, 3 pages.
Notice of Publication mailed Sep. 13, 2007 for U.S. Appl. No. 11/565,553, 1 page.
Restriction Requirement mailed Dec. 7, 2009 for U.S. Appl. No. 11/565,553, 7 pages.
Response to Restriction Requirement mailed Feb. 8, 2010 for U.S. Appl. No. 11/565,553, 18 pages.
Office Action mailed May 12, 2010 for U.S. Appl. No. 11/565,553, 18 pages.
Interview Summary mailed Aug. 4, 2010 for U.S. Appl. No. 11/565,553, 3 pages.
Office Action Response mailed Aug. 12, 2010 for U.S. Appl. No. 11/565,553, 27 pages.
Application as filed (U.S. Appl. No. 11/325,388, filed Jan. 3, 2006), 66 pages.
Notice to file missing parts mailed Feb. 17, 2006 for U.S. Appl. No. 11/325,388, 2 pages.
Response to notice to file missing parts mailed Feb. 17, 2006 for U.S. Appl. No. 11/325,388, 17 pages.
Restriction Requirement mailed Dec. 8, 2009 for U.S. Appl. No. 11/325,388, 7 pages.
Response to Restriction Requirement mailed Feb. 8, 2010 for U.S. Appl. No. 11/325,388 for U.S. Appl. No. 11/325,388, 13 pages.
Office Action mailed Apr. 27, 2010 for U.S. Appl. No. 11/325,388, 21 pages.
Office Action Response and Terminal Disclaimer mailed Jul. 27, 2010 for U.S. Appl. No. 11/325,388, 30 pages.
Notice of Non-Compliant Amendment mailed Aug. 3, 2010 for U.S. Appl. No. 11/325,388, 2 pages.
Interview Summary mailed Aug. 5, 2010 for U.S. Appl. No. 11/325,388, 3 pages.

Decision on Terminal Disclaimer mailed Aug. 27, 2010 for U.S. Appl. No. 11/325,388, 3 pages.
Office Action Response mailed Sep. 3, 2010 for U.S. Appl. No. 11/325,388, 27 pages.
Application as filed (U.S. Appl. No. 11/508,669, filed Aug. 22, 2006), 108 pages.
Notice to file missing parts mailed Sep. 8, 2006 for U.S. Appl. No. 11/508,669, 2 pages.
Response to notice to file missing parts mailed Jan. 8, 2007 for U.S. Appl. No. 11/508,669, 7 pages.
Filing Receipt and Notice of Informal Application mailed Jan. 16, 2007 for U.S. Appl. No. 11/508,669, 4 pages.
Petition under 37 C.F.R. 1.78 and Preliminary Amendment mailed Jun. 4, 2007 for U.S. Appl. No. 11/508,669, 6 pages.
Notice of Publication mailed Jul. 5, 2007 for U.S. Appl. No. 11/508,669, 1 page.
Corrected Filing Receipt mailed Aug. 9, 2007 for U.S. Appl. No. 11/508,669, 3 pages.
Decision for Petition under 37 C.F.R. 1.78 and Corrected Filing Receipt mailed Aug. 13, 2007 for U.S. Appl. No. 11/508,669, 10 pages.
Notice of Publication mailed Dec. 20, 2007 for U.S. Appl. No. 11/508,669, 1 page.
Restriction Requirement mailed Dec. 8, 2009 for U.S. Appl. No. 11/508,669, 8 pages.
Response to Restriction Requirement mailed Feb. 8, 2010 for U.S. Appl. No. 11/508,669, 20 pages.
Office Action mailed Apr. 28, 2010 for U.S. Appl. No. 11/508,669, 12 pages.
Office Action Response and Terminal Disclaimer mailed Jul. 28, 2010 for U.S. Appl. No. 11/508,669, 36 pages.
Interview Summary mailed Aug. 4, 2010 for U.S. Appl. No. 11/508,669, 4 pages.
Decision on Terminal Disclaimer mailed Sep. 1, 2010 for U.S. Appl. No. 11/508,669, 1 page.
Final Office Action mailed Oct. 26, 2010 for U.S. Appl. No. 11/508,669, 11 pages.
Written Opinion mailed Sep. 13, 2005 for PCT/US04/023533, 3 pages.
Publication of Application mailed Oct. 13, 2005 for PCT/US04/023533, 49 pages.
Article 19 Publication mailed Dec. 29, 2005 for PCT/US04/023533, 6 pages.
Preliminary Report on Patentability for PCT/US04/023533, 4 pages.
EP Filing Documents for EP National stage mailed Oct. 9, 2006 for EP04778857.5, 7 pages.
Publication Notice mailed Nov. 15, 2006 for EP04778857.5, 1 page.
European Search Report mailed Mar. 27, 2007 for EP04778857.5, 5 pages.
Official Letter from EPO mailed Jul. 27, 2007 for EP04778857.5, 1 page.
Article 94(3) communication mailed Feb. 20, 2008 for EP04778857.5, 8 pages.
Application as field, mailed Jan. 3, 2007 for PCT/US07/060056, 68 pages.
Notification concerning Submission or Transmittal of Priority Document mailed Jun. 14, 2007 for PCT/US07/060056, 1 page.
Publication of ISR mailed Aug. 2, 2007 for PCT/US07/060056, 2 pages.
Entry into EP phase mailed Jun. 6, 2008 for PCT/US07/060056, 3 pages.
Written Opinion mailed Jul. 16, 2008 for PCT/US07/060056, 9 pages.
Notification Concerning Transmittal of International Preliminary Report of Patentability for PCT/US07/060056, 2 pages.
Non-Final Office Action response, mailed Aug. 23, 2011 for U.S. Appl. No. 11/506,564, 27 pages.
Non-Final Office Action response, mailed Sep. 9, 2011 for U.S. Appl. No. 11/325,388, 43 pages.
Non-Final Office Action, mailed Aug. 4, 2011 for U.S. Appl. No. 11/508,669, 11 pages.
Written Opinion for Application No. PCT/US2004/023533, Sep. 13, 2005, 3 pages.
Notification Concerning Transmittal of International Preliminary Report on Patentability for Application No. PCT/US2004/023533, Sep. 21, 2006 2 pages.
Second and Supplementary Notice Informing the Applicant of the Communication of the International Application for Application No. PCT/US2004/023533, Jul. 13, 2006, 1 page.
Communication Rule 51(2) for Application No. 04778857.5, Sep. 3, 2008, 1 page.
Noting a Loss of Rights for Application No. 04778857.5, May 8, 2008, 1 page.
Notice of Allowance and issue fee dues, mailed Jan. 20, 2012, for U.S. Appl. No. 11/506,564, 15 pages.
Final Office Action, mailed Feb. 29, 2012 for U.S. Appl. No. 11/325,388, 27 pages.
Non-Final Office Action Response mailed Jan. 4, 2012 for U.S. Appl. No. 11/508,669, 38 pages.
Final Office Action, mailed Mar. 14, 2012 for U.S. Appl. No. 11/508,669, 14 pages.

* cited by examiner

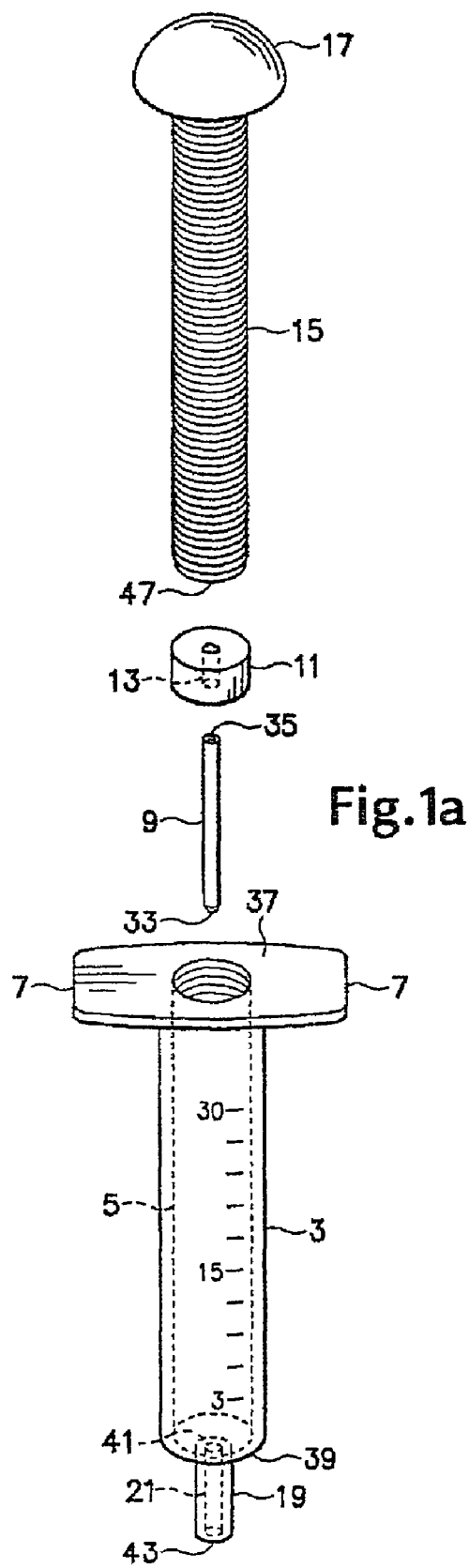

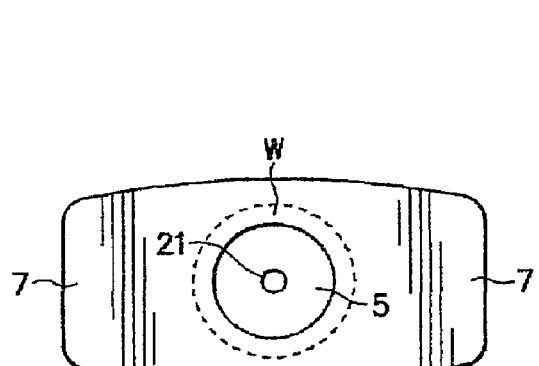
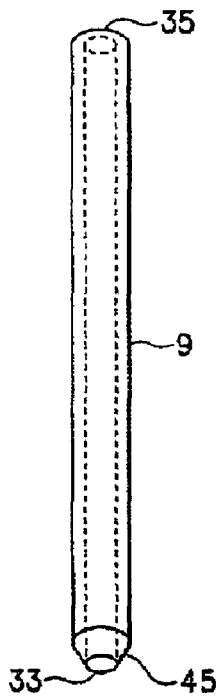
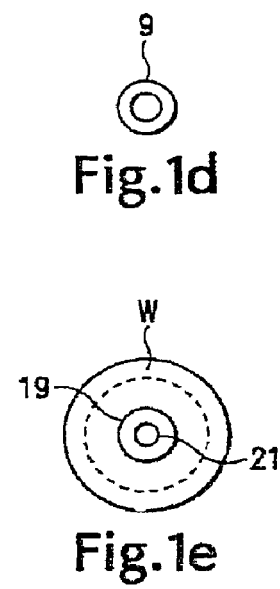
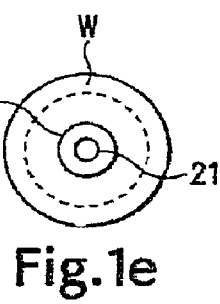
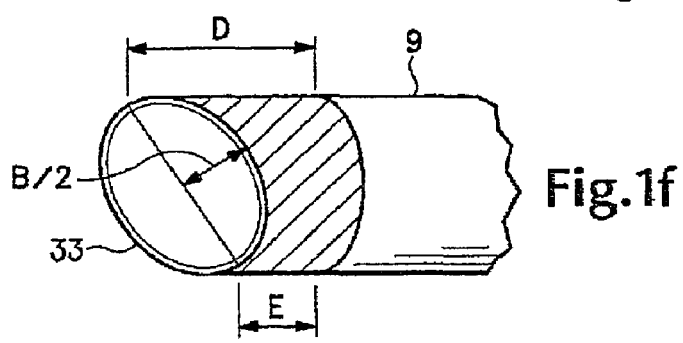
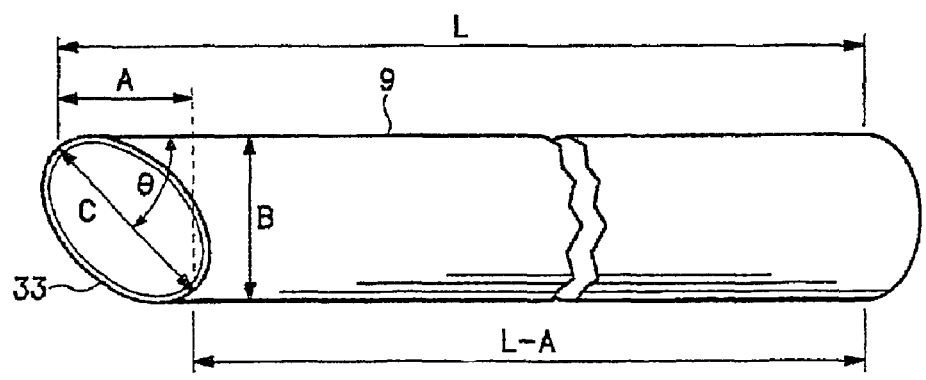

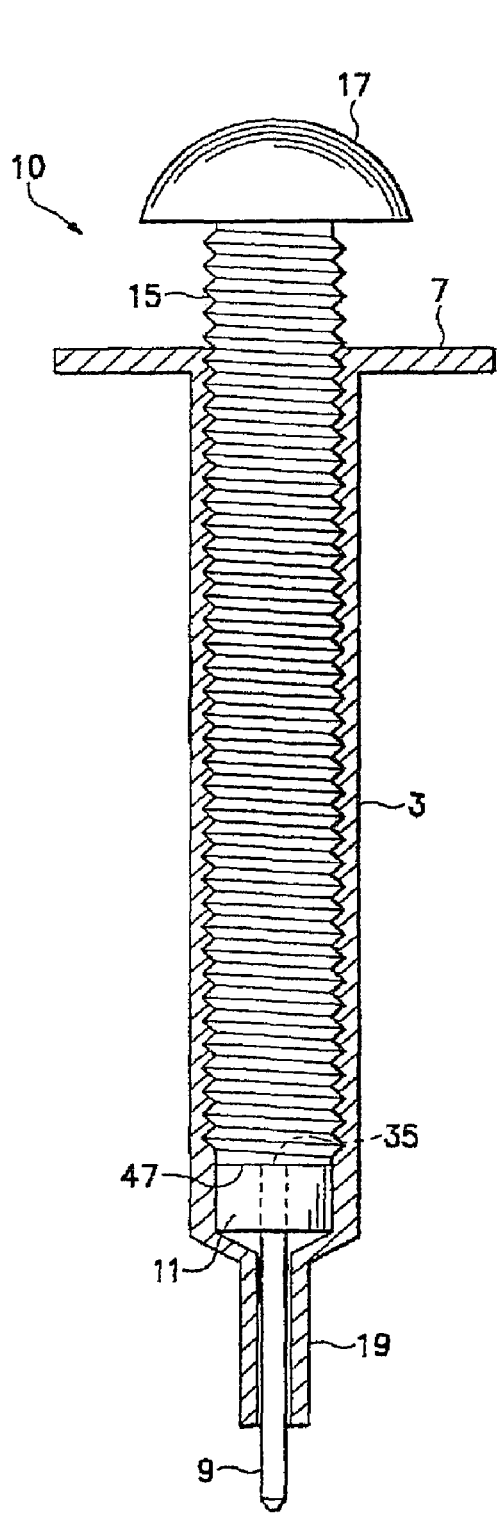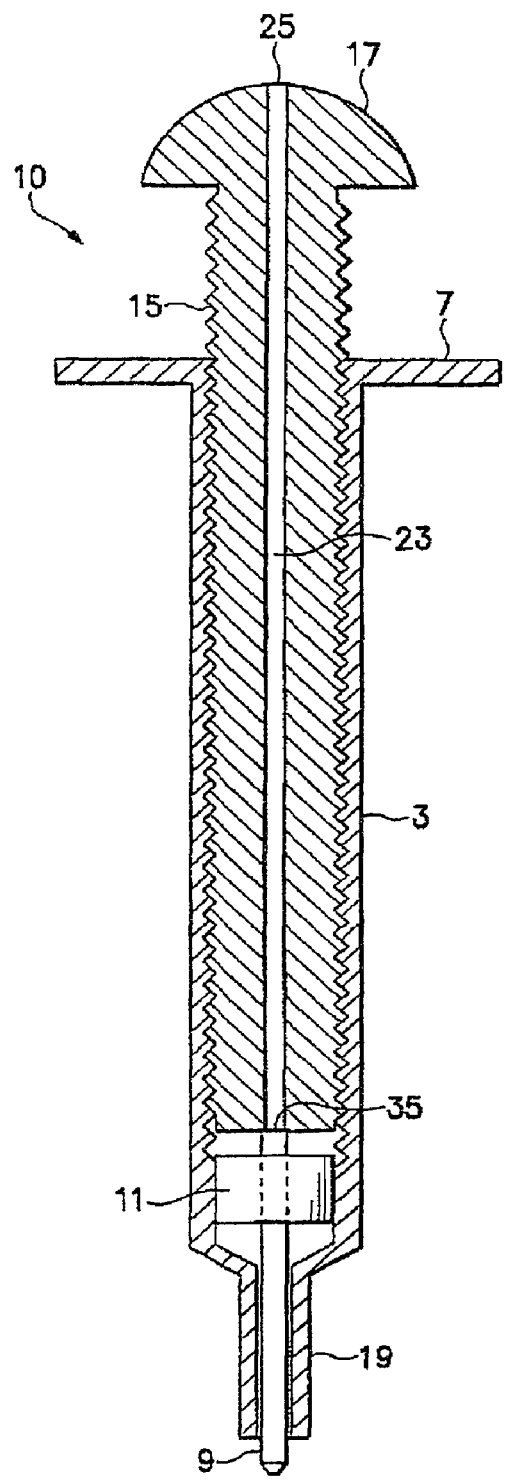

FOLLICULAR EXTRACTION PUNCH AND METHOD

CROSS-REFERENCE TO RELATED APPLICATION

The present application is a continuation-in-part of U.S. application Ser. No. 10/795,835 filed Mar. 9, 2004 titled, "Follicular Extraction Device and Method" by John P. Cole, now U.S. Pat. No. 7,172,604.

TECHNICAL FIELD

This invention relates generally to surgical instruments useful for extracting live hair follicles from mammalian subjects for transplantation on other parts of the body of such subjects. More specifically, the invention provides a surgical instrument useful for extracting live hair follicles from human skin for transplantation to other portions of the skin, such as the scalp. An instrument according to the invention precisely controls the depth to which an incision is made during the follicular extraction process.

BACKGROUND

The prior art contains numerous examples of instruments useful for extracting live hair follicles from the skin of human subjects, and methods associated with the use thereof. U.S. Pat. No. 4,476,864 teaches a light weight, portable, hand held power actuated hair transplant plug cutting device that is capable of making either simultaneous multiple punches or a single punch in the scalp of a patient. In the device, a single shaft member with a removable cutting tip extends through one wall of the housing unit, while a plurality of shaft members with removable cutting tips extends through the opposite wall of the housing unit. Actuation of a power drive causes rotation of both the single shaft member and the plurality of shaft members so that only the single cutting device is needed to make all of the punches required for the hair transplant operation. Tools are also provided for placing and removing disposable cutting tips on and from the shaft members. U.S. Pat. No. 5,507,765 describes a punch-type surgical instrument for skin incision along a closed line, such as a substantially elliptical line, that includes a handle, a blade unit and a means for attaching the handle to the blade unit in a way which achieves high stability between the handle and blade unit and which allows the two parts to be made as ones easily connectable to and dis-connectable from one another. The blade unit may be made and furnished in different sizes to cause the instrument to be one selectably variable in size. U.S. Pat. No. 5,578,054 sets forth a method for transplanting hair, which method comprises: a) inserting an instrument having a shaft with a proximal end, a sharpened distal end forming a blade thereon, and a longitudinal axis extending between the proximal end and the distal end, into the skin to a pre-selected depth as determined by a stop disposed along the shaft to form an incision, wherein the blade is normal to the longitudinal axis of the shaft, and wherein the stop prevents the blade from extending beyond about 5 mm into the scalp, and wherein the distance between the blade and the stop is adjusted before inserting the blade; b) removing the instrument from the skin; and c) placing a graft of skin having at least one hair into the incision. U.S. Pat. No. 5,766,177 provides a rongeur which comprises: a) a body having a distal end, a tubular portion and a proximal end, wherein the body at the distal end includes an elongated member terminating in an anvil and at the proximal end terminating in handle means; b) a tubular cutting member, wherein the cutting member is movable within and guided by the tubular portion and extending beyond the body at the proximal end; and c) a means for actuating the cutting member to cut bodily material placed between the anvil and the distal end of the cutting member. U.S. Pat. No. 5,792,169 discloses an instrument for placement of hair grafts in the tissue of a patient, comprising: a) a first plate comprising a base member having a number of first bores passing therethrough, and a number of hollow first catheters extending therefrom and aligned with the first bores; b) a second plate comprising a base having a number of first spikes extending therefrom, the spikes arranged and sized for location within the first catheters; c) a third plate having a base with a number of second bores passing therethrough and a number of hollow second catheters extending therefrom and aligned with the second bores, the second catheters sized for location within the first catheters; and d) a fourth plate having a base with a number of second spikes extending therefrom, wherein the second spikes are arranged and sized for location within the second catheters. U.S. Pat. No. 5,817,120 teaches an instrument for implanting hair grafts into a patient's scalp, comprising: a) an elongate housing adapted to be manipulated by a surgeon during implanting of the hair grafts, wherein the elongate housing has a throughbore extending at least partway therealong from a first end thereof, and having a slot defining a slotted loading position adjacent to the throughbore for loading hair grafts into the instrument; b) a cutting device affixed to the first end of the elongate housing by which the surgeon may make an incision in the patient's scalp, into which a hair graft is to be implanted; and c) an implanting member, disposed axially movably within the throughbore of the elongate housing, wherein the implanting member includes a forwardly projecting finger. The implanting member is movable from a first position in which the finger is positioned adjacent to the slotted loading position so as to be able to load a hair graft, to a second position in which a loaded hair graft is bounded between the finger and the cutting device, and to a third position in which the finger extends beyond the cutting device. U.S. Pat. No. 5,895,403 describes a surgical cutting tool with vacuum clearance capability, comprising a length of cylindrical surgical steel having an axial bore therethrough, a proximal end cutting tip terminating in a cutting edge, and a distal end. The axial bore has a first inside diameter at the cutting edge, a second inside diameter greater than the first inside diameter forming a first relief near the cutting edge, and a third inside diameter greater than the second inside diameter forming a second relief upstream of the first relief. As vacuum is applied at the distal end of the tool, tissue plugs cut at the cutting edge pass easily through the first and second reliefs to exit the axial bore.

However, of all the prior art, none has thus far provided an instrument through the use of which the precise depth of incision is repeatedly and precisely controlled to result in the vast majority of follicles extracted to continue to furnish hair at the new site to which they are transplanted. The present invention provides such an instrument, which is also simplistic in design and easy to use by the skilled practitioner.

SUMMARY OF THE INVENTION

The present invention provides an instrument useful for extracting live hair follicles from mammalian skin tissue, which device comprises a main body portion having a first end portion, a second end portion, and a longest length dimension. The main body portion further comprises a first bore centrally disposed therethrough, wherein the axis of the first bore runs parallel to the longest length dimension of the main body portion. The first bore comprises an inner surface within the main body. There is a nipple end portion having a first end portion and a tip portion, which nipple end portion further includes a second bore centrally disposed therethrough. The first end portion of the nipple end portion is attached to the second end portion of the main body portion, and the second bore comprises an inner surface within the nipple end. There is a tubular punch means having a first end portion and a sharp end portion. In one preferred form of the invention, the tubular punch exists substantially in the form of a hollow cylinder having an interior space and an outer diameter, wherein the outer diameter of the tubular punch means is slightly larger than the inner diameter of the second bore, and wherein the tubular punch means is slidably disposed within the second bore, so as to provide a slight interference fit. There is a stabilizer means disposed within the first bore and in contact with the first end portion of the tubular punch means. There is an adjustment screw comprising a threaded outer surface and an end. The adjustment screw is disposed within the first bore such that its threaded outer surface is in contact with the inner surface within the main body. The end of the adjustment screw is in contact with the stabilizer. According to one preferred form of the invention, the stabilizer includes a third bore disposed therethrough that is adapted to receive the first end portion of the tubular punch means. In one embodiment, the first end portion of the tubular punch means is disposed within the third bore through the stabilizer means such that the stabilizer means and the tubular punch means are both slidably disposed as a unit within the first bore and the second bore respectively. In one preferred form of the invention, the adjustment screw includes a head portion and an end portion, and further comprises a fourth bore centrally disposed through its length. The fourth bore may extend from the head portion to the end portion. Thus, in one form of the invention, the interior space within the tubular punch means is in fluid communication with the fourth bore disposed within the adjustment screw.

Yet another embodiment of the invention provides that the first bore extends from the first end portion to the second end portion of the main body portion. In yet another embodiment of the invention the main body portion is substantially cylindrically shaped. In yet another embodiment of the invention the tubular punch means has an outer surface, and the outer surface of the tubular punch means is in contact with the inner surface of the second bore disposed within the nipple end portion. In yet another embodiment of the invention the nipple end portion is substantially cylindrically shaped. In yet another embodiment of the invention the first bore and the second bore have the same diameter. In yet another embodiment of the invention the diameter of the second bore is less than the diameter of the first bore. In yet another embodiment of the invention the diameter of the second bore is greater than the diameter of the first bore. In yet another embodiment of the invention the outer diameter of the tubular punch means is smaller than the inner diameter of the second bore. In yet another embodiment of the invention the nipple end and main body comprise a single construct, and are a single article comprising a plastic, which is made using an injection molding process. In yet another embodiment of the invention the sharp end of the tubular punch means comprises a beveled edge. In yet another embodiment of the invention the stabilizer means is comprised of an elastomeric material selected from the group consisting of: polyolefin homopolymers, polyolefin copolymers, thermoplastic vulcanizates, and thermoset elastomers. In yet another embodiment of the invention the tubular punch means is metallic. In yet another embodiment of the invention the tubular punch means further includes an inner diameter which is substantially uniform along the entire length of the tubular punch means. In one preferred form of the invention the inner diameter of the tubular punch means is any diameter in the range of between about 0.5 millimeters and about 4.5 millimeters. In one preferred embodiment of the invention the nipple end portion comprises a flat surface which is adapted to contact the skin of a patient, and the total surface area of the nipple end which contacts the patient is in the range of between about 5 square millimeters and about 25 square millimeters.

In a more general sense, the invention provides an instrument useful for extracting live hair follicles from mammalian skin tissue, which device comprises: a nipple end portion having a first end portion and a tip portion. The nipple end portion has a longest length dimension and further includes a bore disposed therethrough whose axis is parallel to the longest length dimension. The bore comprises an inner surface within the nipple end. There is a tubular punch means which exists substantially in the form of a hollow cylinder having two open ends, an interior space, and an outer diameter not exceeding about 5.0 millimeters. At least one end of the tubular punch means is a cutting end which is capable of piercing the skin. The tubular punch means further includes an inner diameter between about 0.5 millimeters and 4.5 millimeters, which is substantially uniform along the entire length of the tubular punch means. The tubular punch means is slidably disposed within the bore such that its cutting end is capable of coinciding with the tip portion of the nipple end portion when the tubular punch means does not protrude outward from the tip portion. There is a means for adjusting the position of the tubular punch means within the bore, including control of the amount which the cutting end protrudes from the tip portion of the nipple end portion. The nipple end portion may comprise a flat surface which is adapted to contact the skin of a patient, wherein the total surface area of the nipple end which contacts the patient is in the range of between about 5 and about 25 square millimeters. According to one preferred form of the invention, the means for adjusting the position of the tubular punch means within the bore comprises a threaded screw having an end portion which is in effective mechanical contact with the tubular punch means, and a stationary portion capable of engaging with the threads on the screw, wherein the stationary portion is in effective mechanical contact with the nipple end portion. In one form of the invention, such means includes the main body portion 3, adjustment screw 15, and stabilizer 11, as described elsewhere herein.

The invention further provides a process for extracting a live hair follicle from a mammalian subject comprising the steps of: a) providing a tubular punch means which exists substantially in the form of a hollow cylinder having and axis, a first open end, a second open end, an interior space, and an outer diameter not exceeding about 2.0 millimeters, wherein the first end of the tubular punch means is a cutting end which is capable of piercing the skin; b) contacting the cutting end to the skin of a mammalian subject, such that a hair on the skin of the mammalian subject is disposed within the interior space, and such that the axis of the cylinder is disposed at a first angle with respect to the surface of the skin of the subject, wherein the first angle is between about 85 degrees and 95 degrees; c) causing the cutting end to penetrate the skin of the subject to a depth of at least 0.05 millimeters but no greater than about 0.3 millimeters; d) tilting the tubular punch means so that it is disposed at a second angle with respect to the surface of the skin of the subject, which second angle is any angle between about 20 degrees and about 70 degrees; e) causing the cutting end to further penetrate the skin of the subject to a depth of at least 1 millimeter but no greater than about 7 millimeters (with an average of about 4.15 mm) while maintaining the tubular punch means at the second angle with respect to the surface of the skin of the subject and while maintaining the hair within the interior space so as to cause to follicle within which the hair grows to be disposed within the interior space; and f) removing the follicle from the subject. In a preferred process according to the invention, the first angle is about 90 degrees and wherein the second angle is about 56 degrees or the corresponding acute angle of hair growth to the surface of the skin. According to one preferred process according to the invention, the step of removing the follicle from the subject comprises applying a vacuum to the second end of the tubular punch means, or may be accomplished by cutting the follicle from the subject using a sharp instrument, such as a scalpel or modified scalpel, which is available from the instant inventor.

BRIEF DESCRIPTION OF THE DRAWINGS

FIG. 1a shows an exploded perspective view of the various components of a tool according to the invention;

FIG. 1b shows an overhead view of the body portion 3 of a tool according to one preferred form of the invention;

FIG. 1c shows a perspective view of a tubular punch means element of a tool according to the invention;

FIG. 1d shows an end view of the tubular punch means element of the invention;

FIG. 1e shows an end view of the main body portion of an instrument according to the invention as viewed from the nipple end perspective;

FIG. 1f shows a side perspective view of a tubular punch means according to an alternate form of the invention; FIG. 1g shows a side perspective view of a tubular punch means according to an alternate form of the invention;

FIG. 2 shows a cutaway view of a tool according to the invention in its assembled form;

FIG. 3 shows a cutaway view of a tool according to an alternate form of the invention in its assembled form;

DETAILED DESCRIPTION

Figure 4:
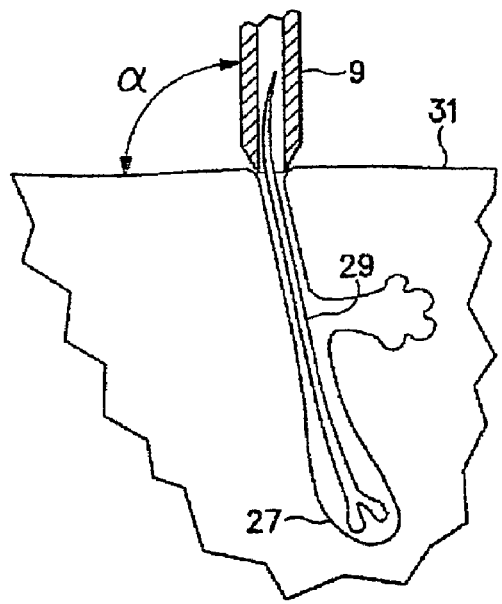
FIG. 4 shows a section of skin containing a hair follicle in contact with a portion of a tool according to the invention.

Referring to the drawings and initially to FIG. 1a there is shown an exploded perspective view of the various components of a tool according to the invention, including the main body portion 3, tubular punch means 9, stabilizer means 11, and adjusting screw 15. The main body portion 3 in a preferred form of the invention is a construct which is substantially cylindrically shaped, having an open first end portion 37 and a second end portion 39. The main body portion 3 further includes a bore 5 centrally disposed therewithin along its longest length dimension, which bore in one preferred form of the invention extends from the first end portion 37 to the second end portion 39. The walls of the main body portion 3 at the second end portion 39 are tapered inwards towards the axis of the bore 5, and coextensively intersect a nipple end portion 19, which nipple end portion 19 is substantially cylindrically shaped and includes a first end portion 41 and a tip portion 43. Such an arrangement provides for the second end portion 39 of the main body portion 3 to be attached to the nipple end 19 at the first end portion 41 of the nipple end 19. The nipple end 19 includes a bore 21 centrally disposed therewith along its longest length dimension, which bore extends from the first end portion 41 of the nipple end 19 to the tip portion 43 of the nipple end 19, and the bore 5 and bore 21 are thus in fluid communication with one another in a main body portion 3 provided in accordance with a preferred form of the invention. Further, the bore 5 is open to the ambient surroundings at the first end portion 37, and the bore 21 is open to the ambient surroundings at the tip portion 43. The main body portion is thus reminiscent of the body portion of common polyolefin syringes which are in common use in the medical arts. According to a preferred form of the invention, the main body portion 3 and the nipple end 19 are both elements of a single common construction provided for example, by an injection molding process. The length of the nipple end 19 is preferably in the range of between about 0.03 millimeters and about 10 millimeters, with a preferred length of about 6 millimeters. When an instrument according to the invention is fabricated from a plastic material, it is preferred that the bore 21 is slightly smaller than the outside diameter of the tubular punch means 9, to preclude the tubular punch means from motion induced either by the surgeon moving the instrument of the invention around and about, or the influences of gravity. In one form of the invention when the nipple end 19 is fabricated from a polyolefin, it is preferred that the bore 21 within the nipple end 19 is at least about 0.1 millimeter smaller than the outside diameter of the tubular punch means 9.

The main body portion 3 is preferably comprised of a translucent material, such as a thermoplastic polyolefin such as homopolymers of polypropylene or polyethylene, including copolymers of the foregoing with any $C_{1-6}$ olefinic monomer, as such materials are well known to those in the polymer arts. However, other materials of construction including glass, various metals such as stainless steels, etc. are also suitable materials from which the main body portion of a tool according to the invention may be constructed. The main body portion 3 is also preferably provided with graduation markings on its outer surface, to assist in setting the depth of the tubular punch means 9 as is explained later in this specification. The main body portion 3 in a preferred form of the invention also optionally includes a plurality of gripping means 7 disposed at the first end portion 37 of the main body portion 3. These optional gripping means 7 in one form of the invention are flanges which extend perpendicularly with respect to the axis of the bore 5 and overall length dimension of the main body portion 3.

FIG. 1b shows an overhead view of the body portion 3 of a tool according to one preferred form of the invention, as viewed from the first end portion 37 looking down into the bore 5 and showing the respective locations of the gripping means 7, the bore 5, and the thickness W of the wall portion of the main body 3 itself. Also visible in this view is the bore 21 of the nipple end at the far end of the bore 5.

FIG. 1c shows a perspective view of a tubular punch means element 9 of a tool according to the invention. The tubular punch means is a hollow tube, preferably comprised of a metal or metal alloy such as stainless steel or titanium. However, any metal or alloy recognized as being useful for the manufacture of surgical equipment may be used as a raw material from which the tubular punch means 9 is fabricated, including various different grades of stainless steels, and protective coatings subsequently applied thereto, such as titanium, zirconium, coatings, etc., whose use is well known in the art. The tubular punch means 9 includes a first end portion 35 and a sharp end portion 33. The sharp end portion in one preferred form of the invention includes a bevel 45 which is coextensively disposed about the sharp end portion, which constitutes a cutting edge. The tubular punch means 9 in its simplest form a hollow tube which is shaped in the form of a hollow cylinder having an open top portion, an open bottom portion, and a wall portion, with a bore disposed longitudinally therethrough. Preferably, the inside diameter of the tubular punch means 9 is any diameter in the range between about 0.5 millimeters to about 4.5 millimeters, and preferably the outside diameter of the tubular punch means 9 is about 0.2 millimeters to about 0.3 millimeters greater than the inside diameter.

FIG. 1d shows an end view of the tubular punch means 9, and FIG. 1e shows an end view of the main body portion of an instrument according to the invention as viewed from the nipple end perspective, and the respective locations of the nipple end 19 and the bore extending therethrough 21. The thickness of the wall portion W of the main body 3 is also shown. In this FIG. 1e it can be seen that the portion of the nipple end which is intended to contact the skin of the patient is shaped like a donut; stated another way, the portion of the nipple end which contacts the patients' skin is in one preferred form of the invention a substantially planar surface that is bounded by two concentric circles in a preferred form of the invention. Preferably, the total amount of surface area which contacts the skin is in the range of between about 5 square millimeters and about 25 square millimeters, and is obtained by subtracting the surface area of the circle represented by the bore 21 from the surface area of a circular area having the diameter of the nipple end 19, when the nipple end is circular in cross section.

FIG. 1f shows a side perspective view of a tubular punch means 9 according to an alternate form of the invention. In this embodiment, the sharp end 33 of the tubular punch means 9 is shown to be angled. The value of B/2 is about 0.5 millimeters; D is about 1 millimeter, E is about 0.32 millimeters, and the shaded area represents that section of the tubular punch means which preferably comprises titanium, or a titanium coating.

FIG. 1g shows a side perspective view of a tubular punch means according to an alternate form of the invention. In this embodiment, A is about 0.58 millimeters; B is about 1 millimeter; C is about 1.15 millimeters; and the angle theta is about 60 degrees. However, any angle of theta in the range of between about 30 degrees and 90 degrees is within the scope of the present invention.

There is a stabilizer means 11 which in one form of the invention is a solid cylindrical construct made preferably from an elastomeric substance, such as a molded rubber, wherein the stabilizer means 11 has an outside diameter which is slightly greater than or approximately the same size as the diameter of bore 5, to enable the stabilizer means 11 to reside within the bore 5 in a sufficiently snug manner so as to enable the stabilizer means to be retained within the bore 5 in the event that the main body 3 containing the stabilizer means 11 within its bore 5 is inverted and the stabilizer means is subject to normal gravitational forces. In another embodiment, the stabilizer means 11 includes a bore 13 whose axis coincides substantially with the axis of the stabilizer means itself. In such an embodiment, the diameter of the bore 13 is preferably slightly smaller than the outer diameter of the tubular punch means 9 (the diameter of which is uniform along its length), so as to enable the first end portion 35 of the tubular punch means 9 to be retained within the bore 13 within the stabilizer means 11 by a snug interference fit caused to exist by the slight expansion of the elastomeric stabilizer means 11 from the insertion of the tubular punch means in to the bore 11. The bore 13 is preferably centrally disposed within the stabilizer so that the punch means 9 is maintained in a central axis. The stabilizer 11 limits movement of the punch means 9 in a lateral direction within bore 5, and maintains proper alignment of punch means 9 with the angle and direction of hair growth. The stabilizer may be comprised of: polyolefin homopolymers, such as polypropylene or polyethylene; polyolefin copolymers, including ethylene-propylene copolymers, propylene butene copolymers, and propylene-octene copolymers; thermoplastic vulcanizates; and thermoset elastomers.

In FIG. 1a there is also shown an adjustment screw 15, which includes threads on its outer surface, which are of such dimension to cause them to effectively mate with the inner surface of the bore 5 of the body portion 3. The inner wall of the bore 5 of the main body portion 3 may or may not include threads. Thus, in constructing a tool according to the invention, the adjustment screw 15 is inserted into the bore 5 and the adjustment screw 15 is rotated to cause it to reside at a desired depth or location within the bore 5. The adjustment screw 15 includes a head portion 17 which is convenient for a user of an instrument according to the invention to grasp. In one embodiment, the adjustment screw 15 may be coated with tape to improve its contact with bore 5 and to reduce slippage.

FIG. 2 shows an assembled tool 10 according to the invention and illustrating the respective positions of the various elements of the invention including the adjustment screw 15, within the main body 3. The tubular punch means 9 is shown disposed within the bore 21, whose inner diameter is slightly larger than the outside diameter of the tubular punch means 9 so as to enable the nipple end 19 to act as a bearing for movement of the tubular punch means laterally within the bore 21. Stabilizer means 11 is shown disposed between first end portion 35 of the tubular punch and end 39 of the body portion 3 such that it is coextensively disposed about tubular punch 9 at the end of tubular punch 9 closest to end 39 but not in contact with stabilizer 11. Under such an arrangement, turning the adjustment screw inwards into the bore 5 of the main body portion causes the sharp end 33 of the tubular punch means to protrude from the tip portion 43 of the nipple end 19 in an amount proportional to the amount the adjustment screw enters the bore 5 by virtue of its being rotated.

FIG. 3 shows an assembled tool 10 according to an alternate form of the invention and illustrating the respective positions of its various elements including the adjustment screw 15, within the main body 3. In this embodiment, the adjustment screw includes a bore 23 disposed through its center along its entire length, providing a hole 25 to exist at the top of the head portion 17. The head portion 17 can take on a variety of shapes, dimensions, and surface coatings. According to one preferred form of the invention, the width of the head portion 17 is greater than about 9 millimeters. The tubular punch means 9 is shown disposed within the bore 21, whose inner diameter is slightly larger than the outside diameter of the tubular punch means 9 so as to enable the nipple end 19 to act as a guide for movement of the tubular punch means 9 within the bore 21. Stabilizer means 11 is shown disposed between the first end portion 39 of the tubular punch means 9 and the second end portion 39 of the main body portion 3. In this embodiment, the stabilizer means 11 includes a bore 13 as shown in FIG. 1, in which is disposed a section of the tubular punch means. Thus, the interior space within the tubular punch means in this embodiment is in fluid communication with the hollow interior space within the bore 23, which also means that the space within the hole 25 is in fluid communication with the most distal (tip) portion of the tubular punch means 9. This provision enables a vacuum source to be selectively applied to the hole at 25 to assist in the successful extraction of a follicle, blood, fluid, or serum through use of the device 10. Again, turning the adjustment screw inwards into the bore of the main body portion 3 causes the sharp end 33 of the tubular punch means to protrude from the tip portion 43 of the nipple end 19 in an amount proportional to the amount the adjustment screw enters the bore 5 by virtue of its being rotated.

The assembly of an instrument according to the invention is a straightforward undertaking. First, the main body portion 3 is provided. Next, the tubular punch means 9 and stabilizer means 11 are caused to reside at their earlier-specified locations within the bores 21 and 5 respectively. This may be accomplished by first placing the tubular punch means into the bore 21, and separately placing the stabilizer means 11 into the opening at the first end portion 37 of the main body portion and forcing it downwards (such as with a rigid rod such as a pencil, screwdriver, etc.) into the bore 5 until the stabilizer means 11 comes into contact with the tubular punch means. Alternatively, as mentioned above, the stabilizer means 11 itself may be provided with a bore 13 into which the dull end of the tubular punch means 9 is first partially inserted, thus forming a sub-assembly consisting of the tubular punch means 9 and stabilizer means 11. This sub-assembly may then be placed into the opening at the first end portion 37 of the main body portion 3 with the tubular punch means 9 end of the sub-assembly being inserted first and forced downwards, taking care that the tubular punch means enters the bore 21 as the sub-assembly approaches the second end portion 39 of the main body 3. Subsequent to the placement of the tubular punch means 9 and stabilizer means 11 at their respective locations within the main body portion, the adjustment screw 15 is next placed into the bore 5, preferably by turning the screw head 17 or other convenient grasping means for manipulating the rotational motion of the adjustment screw. The adjustment screw is caused to enter the bore to a depth at which it just first touches the stabilizer means, and then care is taken to continue slowly admitting more of the screw into the bore so as to cause the sharp end portion of the tubular punch means 9 to be just flush with the distal end of the nipple end 19. In accordance with the use of an instrument according to the invention, it will be found necessary at times to precisely adjust the distance or amount that the end portion of the tubular punch means 9 protrudes from the end of the nipple end 19, as it is shown to do so a distance denoted D in FIG. 7, as later explained. Turning the adjustment screw 15 is thus useful in accomplishing the task of forcing the tubular punch means 9 out of the nipple end 19 a precise desired amount, as is necessary to provide statistically large proportions of hair grafts having a high probability of survival, which may often be greater than such numbers provided by many, if not all, devices of the prior art having similar intended functions. This action is assisted using the presence of graduation marks disposed along the translucent main body 3 as a guide. The graduation marks may be printed on through the use of inks or etchings, or may be milled or ground into the body 3 itself.

Although the stabilizer means 11 is shown in one location within the bore 5 in FIG. 1a and at another location in FIG. 3, and is thus moveable within the bore 5, it is within the scope of the present invention that the stabilizer means 11 is disposed in a stationary position within the bore, at any location within the bore 5. According to one preferred form of the invention, the stabilizer means 11 is bottomed out within the bore 5 at a position which represents its furthest possible travel position against the nipple end portion 19. In addition, it is within the scope of the present invention that the tubular punch means 9 is slidably disposed with respect to the stabilizer means 11, i.e., in one embodiment the tubular punch means may move with respect to the stabilizer means 11 by motion through the bore 13, and in another embodiment the tubular punch means 9 is not moveable with respect to the stabilizer means 11, especially in the embodiment when the stabilizer means 11 is not fixed in a stationary position within the bore 5. It is especially preferred that the user be able to visually observe the first end portion 35 of the tubular punch means 9 within the bore 5, and towards this end it is preferred that the material from which the main body portion 3 is comprised to be visually translucent or to comprise a window to enable such observation. In FIG. 3 is shown the first end portion 35 of the tubular punch means 9 in contact with the end 47 of the adjusting screw 15. In one embodiment the diameter of the bore 23 through the adjustment screw is larger than the outer diameter of the tubular punch means 9. In another embodiment, the diameter of the bore 23 through the adjustment screw is smaller than the outer diameter of the tubular punch means 9. In another embodiment, the diameter of the bore 23 through the adjustment screw is substantially equivalent to the outer diameter of the tubular punch means 9. In another embodiment, the diameter of the bore 23 through the adjustment screw is larger than the outer diameter of the tubular punch means 9 and the tubular punch means 9 protrudes above the surface of the stabilizer means 11 only slightly, so as to enable the stabilizer means 11 to function as a gasket in providing a tight seal between the inner space within the tubular punch means 9 and the bore 23. The end portion 35 of the tubular punch means may be disposed within the bore 23.

FIG. 4 shows a section of skin 31 containing a hair follicle 27 with a hair 29 disposed therein, wherein the surface of the skin is in contact with the tubular punch means 9 portion of a tool according to the invention. This FIG. 4 illustrates the first step in illustrating generally a process for extracting a live hair follicle from the skin using an instrument according to the invention as a tool. In this first step, which may be called the initial alignment step, the tubular punch menu 9, after its having been caused to protrude from the nipple end 19 of an instrument according to the invention a pre-determined amount, is contacted with the skin at an angle alpha of approximately. 90 degrees with respect to the skin's surface, over the location at which a hair 29 is growing out of the skin while attempting to keep the hair centered in the bore of the tubular punch means 9. This angle is preferably 90 degrees to the surface of the skin, but may be any angle between about 80 and 100 degrees. An initial incision substantially perpendicular to the skin may result in a smaller incision surface area and may reduce the overall surface area of scar tissue.

Figure 5:
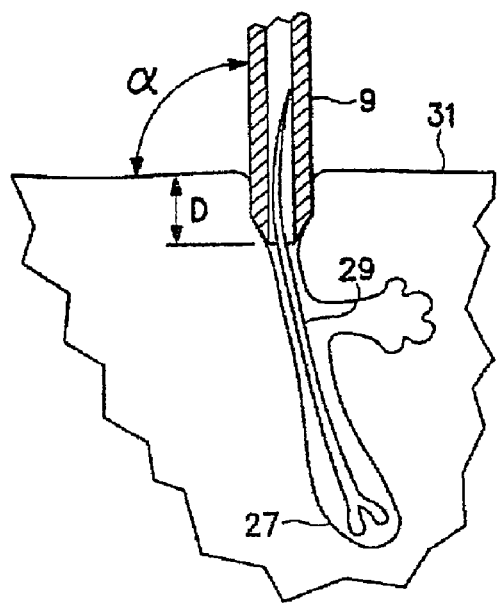
FIG. 5 shows a section of skin containing a hair follicle in contact with a portion of a tool according to the invention.
Figure 6:
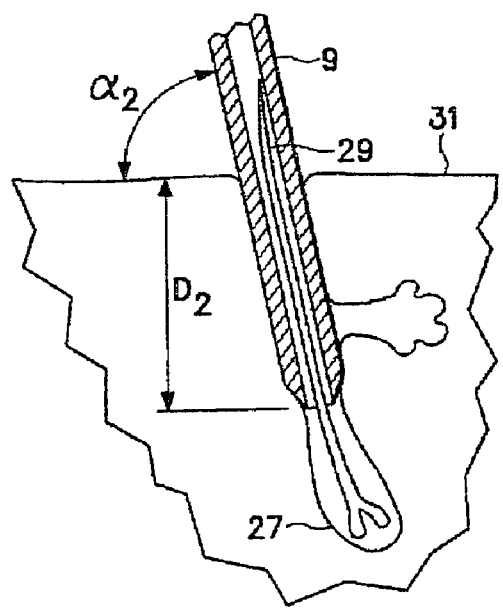
FIG. 6 shows a section of skin containing a hair follicle in contact with a portion of a tool according to the invention.

Next, as shown in FIG. 5, the sharp end portion 33 of the tubular punch means 9 is caused to penetrate the skin over the location at which a hair 29 is growing, an amount equal to the distance denoted D, while the angle alpha with which the tubular punch means 9 is disposed with respect to the skin's surface is maintained at an angle between about 80 and about 100 degrees with an angle alpha of 90 degrees being especially preferred. The distance D is preferably any distance between about 0.05 millimeters and 0.5 millimeters with a depth D of about 0.2 millimeters typically being most preferred when proceeding according to this initial penetration step of the instant method. After the initial penetration step has been accomplished and the sharp end of the tubular punch means 9 has penetrated the skin to the desired depth within the above range, the device of the invention, in the hands of a skilled surgeon, is next precisely angled by the surgeon while still at depth D to an angle of orientation such as that shown in FIG. 6 as alpha-2, and the tubular punch means is inserted into the dermis to a second depth D2 while the tubular punch means 9 is maintained at the precise depth angle denoted as alpha-2 during the entire timespan of the insertion to the new depth D2, while ensuring that the incision is along the same axis as the hair growth. All follicular clusters that consist of more than one hair will have splaying or widening of the distance between the hairs as the hairs enter the skin surface, which is similar to a vase containing a cluster or plurality of stemmed flowers, in which the clusters of flowers narrows at the neck of the vase, which corresponds to the follicular canal for multiple hairs comprising a follicular group. Like a vase of flowers, the distance between stems (or the hairs) becomes more random and wider as the flowers (or hairs) proceed to their maximal depth. A tubular punch means of one millimeter diameter will not fit around all the hairs if the splaying is great or if the number of hairs in the follicular groups is large. Therefore, it is very important to limit the depth of the incision. Making an incision so deep that the hairs within the follicular cluster no longer fit inside the inside diameter of the tubular punch means 9 will result in cutting one or more hair follicles into two segments or a "transection".

The insertion of the tubular punch means 9 into the skin may occur by applying a straight pressure to the device as a whole and is accomplished by the sharp end of the tubular punch means 9 cutting its way through the skin; alternatively, the entire device may be rotated, oscillated and/or moved in a reciprocating fashion or some combination thereof while under slight force by the surgeon during the insertion. The depth D2 may be any depth in the range of about 2 millimeters to about 7 millimeters, with the preferred depth of D2 being typically about 3.8 millimeters. Once the critical depth D2 has been reached, the follicles may be removed by gently tugging on the top of the follicles so that the follicular group is removed in its entirety or the follicular cluster is teased out, using sharp dissection with a surgical needle, a modified scalpel available from the present inventor, or a hair extractor forecep available from the present inventor. Application of a vacuum to hole 25 is instrumental in assisting removal of follicles and/or follicular groups. The critical depth is important to the success of a procedure according to the invention because if the depth is too shallow, it will be very difficult to remove the follicles. On the other hand, if the depth is too deep, the risk of follicular damage including transection becomes detrimentally significant.

Owing to variance amongst individuals within a race or class of mammalian species with respect to the ultimate average depth of their hair follicles and root below the surface of the skin, and also depending on the location of the hair follicles on the body, I have discovered that by precisely controlling the amount which the tubular punch means 9 protrudes from the nipple end 19 of the device of this invention, that great reproducibility of consistency of hair follicles extracted having identical depths is now made possible through the use of my invention. Once the average critical depth of the follicles for a particular individual has been determined, this consistency afforded by my invention allows for the vast majority of follicles extracted using my device and method to survive as fertile potential implants for transplantation to other parts of the same subject's dermal areas, with a success rate exceeding 90% in most cases being readily achievable, which represents a major advance in this art.

Figures 7, 8:
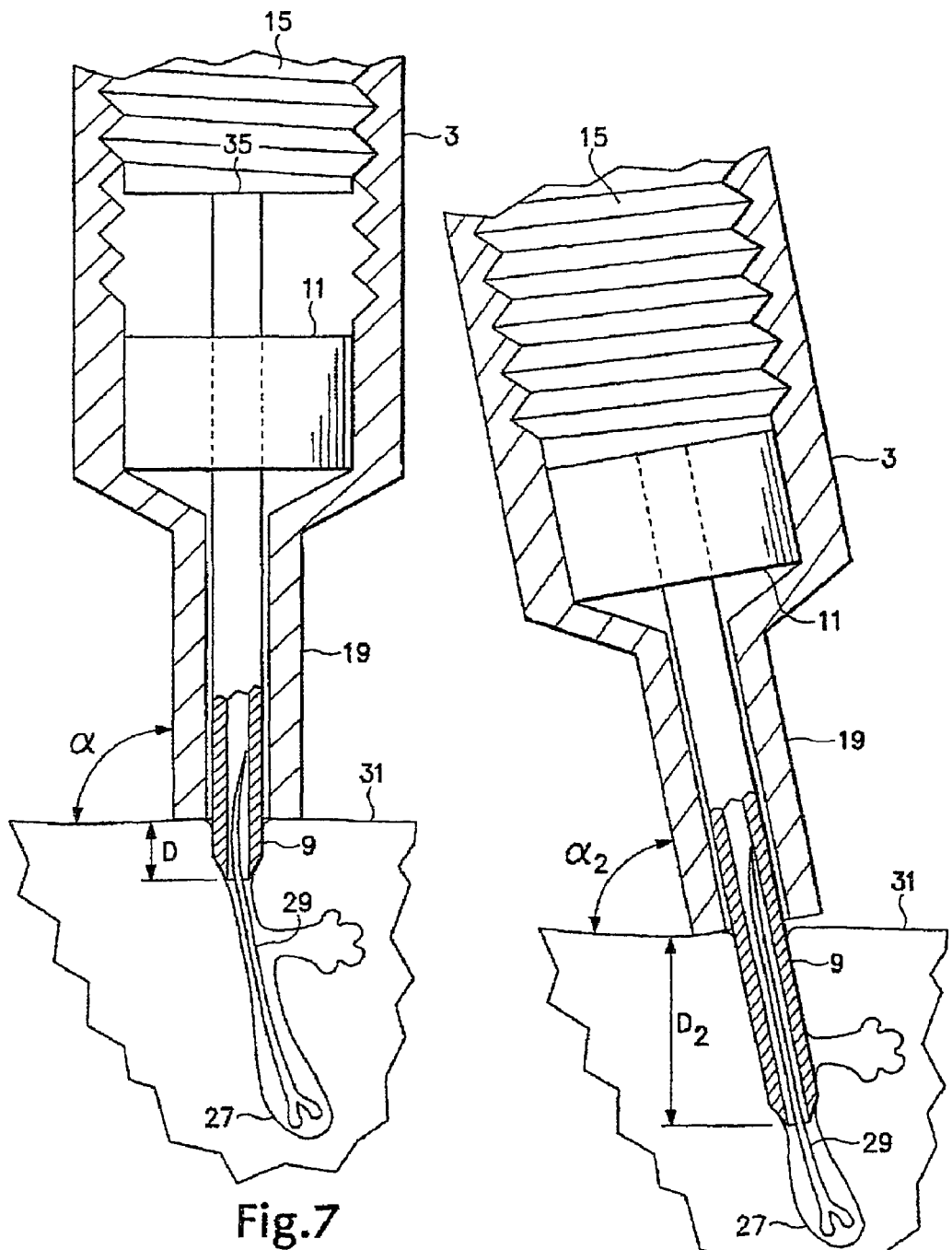
FIG. 7 shows a section of skin containing a hair follicle in contact with a portion of a tool according to the invention.
FIG. 8 shows a section of skin containing a hair follicle in contact with a portion of a tool according to the invention.

In FIG. 7 is shown a section of skin 31 containing a hair follicle 27 in contact with a portion of an instrument according to the invention. In this figure, the initial penetration step has been accomplished, and the sharp end of the tubular punch means 9 has penetrated the skin to the desired depth within the range specified earlier for the depth D. This figure illustrates how the nipple end acts as a stop, in limiting the depth of penetration allowed by the tubular punch means into the skin. The depth of penetration is limited to the amount that the tubular punch means 9 protrudes from the nipple end 19, which is readily controllable by the surgeon by adjusting the adjustment screw 15. In this FIG. 7 is shown the first end portion 35 of the tubular punch means 9 in contact with the end 47 of the adjusting screw 15.

In FIG. 8 is shown a section of skin 31 containing a hair follicle 27 in contact with a portion of an instrument according to the invention. In this figure, the initial penetration step has been accomplished, and the sharp end of the tubular punch means 9 has penetrated the skin to the desired depth within the range specified earlier for the depth D2. This figure also illustrates how the nipple end acts as a stop, in limiting the depth of penetration allowed by the tubular punch means into the skin. The depth of penetration is again seen to be limited to the amount that the tubular punch means 9 protrudes from the nipple end 19, which is readily controllable by the surgeon by adjusting the adjustment screw 15.

In one particularly preferred embodiment, the length of the tubular punch means 9 is 2.5 centimeters in length. The width of the adjustment screw 15 is about 4.5 millimeters and the length of the adjustment screw 15 is about 10 centimeters, and the width of the head portion 17 is about 9 millimeters. However, the head portion 17 could be much wider and have a variety of geometrical shapes, and the present invention includes embodiments wherein the adjustment screw 15 has any length, while enabling the device as a whole to retain its intended functionality. In one form of the invention, the nipple end portion 19 is tapered, and has an outside diameter of about 4.38 millimeters at the top which tapers down to about 4.22 millimeters at the bottom, with an overall length of about 8 millimeters. However, the present invention includes embodiments wherein the nipple end portion is of any length, while enabling the device as a whole to retain its intended functionality. In one preferred form of the invention, the main body portion 3 is about 8 centimeters long, and has a width between about 6.55 millimeters and 6.67 millimeters. However, the present invention includes embodiments wherein the main body portion 3 is of any dimensions, wider, narrower, thinner, thicker, longer or shorter, as prescribed herein, provided that the functionality of the device as specified herein is maintained.

In a particular embodiment, extraction sites and/or tubular punch 9 may be treated with surgical lubricant to decrease friction upon incision into the skin. According to a particular embodiment, surgical lubricant may minimize trauma to the hair follicle and may reduce scarring. In a particular embodiment, an antibiotic ointment may be applied to the incision site to accelerate healing, to reduce the risk of infection and to minimize scarring. After an application of antibiotic ointment, the extraction sites may be treated with a topical steroid to reduce the risk of inflammation and post-inflammatory hypo-pigmentation. Treatment with a topical steroid may also reduce the risk of scarring.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. The present invention further includes all possible combinations of the features recited in the specification and/or any one of the various claims appended hereto with the features recited elsewhere in the specification and/or in any one or more of each of the remaining claims. Accordingly, the presently disclosed invention is intended to cover all such modifications, alterations, and combinations.

What is claimed is:

1. A process comprising:
   providing a tubular punch comprising a hollow cylinder having an axis, a first open end, a second open end, an interior space, and an outer diameter not exceeding about 5.0 millimeters, wherein said first end of said tubular punch comprises a cylindrical cutting end which is capable of piercing skin tissue;
   applying surgical lubricant to said cylindrical cutting end of said tubular punch;
   contacting said cylindrical cutting end to the skin tissue of a mammalian subject, such that a hair on said skin tissue of said mammalian subject is disposed within said interior space, and such that said axis of said cylinder is disposed at a first angle with respect to the surface of said skin tissue of said subject, wherein said first angle is between about 85 degrees and about 95 degrees;
   penetrating said skin tissue of said subject with said cylindrical cutting end to an initial penetration depth of at least about 0.05 millimeters but no greater than about 0.3 millimeters;
   tilting said tubular punch, at least partially in response to said cylindrical cutting end penetrating said skin tissue to said initial penetration depth, so that said tubular punch is disposed at a second angle with respect to said surface of said skin tissue of said subject, which second angle is selected from the group consisting of: any angle between about 20 degrees and about 70 degrees or about an angle of hair growth;
   further penetrating said skin tissue of said subject with said cylindrical cutting end to a selectable depth of at least about 2 millimeters but no greater than about 7 millimeters while substantially maintaining said tubular punch at said second angle with respect to the surface of said skin tissue of said subject and while maintaining said hair within said interior space to cause follicle(s) within which said hair grows to be disposed within said interior space;
   removing said follicle(s) from said subject; and
   treating an incision site with an antibiotic ointment or a topical steroid.

2. A process according to claim 1 wherein said first angle is about 90 degrees and wherein said second angle is about 56 degrees.

3. A process according to claim 1 wherein said removing said follicle from said subject further comprises applying a vacuum to said second end of said tubular punch.

4. A process according to claim 1 wherein said removing said follicle from said subject comprises cutting said follicle from said subject.

5. A process according to claim 1 wherein said second angle substantially coincides with said angle of growth of said hair with respect to the surface of the skin tissue of said subject.

6. A process according to claim 1 wherein said causing said cylindrical cutting end to further penetrate said skin tissue of said subject to a selectable depth comprises turning an adjustment screw component of said tubular punch.

7. A process according to claim 1 wherein said treating an incision site with an antibiotic ointment further comprises applying an antibiotic ointment to said incision site at least 2 days after incision.

8. A process according to claim 1 wherein said treating an incision site with an antibiotic ointment further comprises applying said antibiotic ointment or said topical steroid to said incision site at least around the time of said incision.

9. A method comprising:
   applying surgical lubricant to a cylindrical cutting end of a tubular punch;
   contacting a surface of skin tissue at a first angle with respect to said surface of said skin tissue using said tubular punch;
   making an incision about a hair follicle into said surface of skin tissue using said tubular punch;
   penetrating said skin tissue with said tubular punch to an initial penetration depth of between about 0.05 millimeters and about 0.3 millimeters;
   angling said tubular punch to a second angle with respect to said surface of the skin tissue at least partially in response to said penetrating said skin tissue to said initial penetration depth, wherein said second angle is substantially equal to about an angle of hair growth; and
   penetrating said skin tissue to a selectable depth of between about 2.0 millimeters and about 7.0 millimeters while substantially maintaining said tubular punch at said second angle with respect to said surface of said skin tissue and while maintaining said hair follicle within an interior space of said tubular punch;
   removing said hair follicle from said skin tissue; and
   treating an incision site with an antibiotic ointment or a topical steroid.

10. A method according to claim 9 wherein said first angle is about 90 degrees and wherein said second angle is about 56 degrees.

11. A method according to claim 9 wherein said removing said follicle from said skin tissue further comprises applying a vacuum source to an end of said tubular punch.

12. A method according to claim 9 further comprising;
   moving said tubular punch in at least one or more of the following ways; rotating, oscillating, reciprocating or some combination thereof as said tubular punch is being inserted to said initial penetration depth.

13. A method according to claim 9 further comprising;
   moving said tubular punch in at least one or more of the following ways; rotating, oscillating, reciprocating or some combination thereof as said tubular punch is being inserted to said selectable depth.

14. A method according to claim 9 further comprising treating an incision site with antibiotic ointment at least 2 days after incision.

15. A method according to claim 9 wherein said removing said follicle from said skin tissue further comprises aligning an angled cutting end of a tubular punch with said skin tissue.

16. A method according to claim 9 wherein said causing said cylindrical cutting end to further penetrate said skin tissue of said subject to a selectable depth comprises turning an adjustment screw component of said tubular punch.

17. A method of follicular extraction to reduce scarring comprising:
   applying surgical lubricant to a cylindrical cutting end of a tubular punch;
   contacting a surface of skin tissue at a first angle with respect to said surface of said skin tissue using said tubular punch;

making a first incision about a hair follicle into said surface of skin tissue using said tubular punch;

penetrating said skin tissue with said tubular punch to an initial penetration depth of between about 0.05 millimeters and about 0.3 millimeters;

angling said tubular punch to a second angle with respect to said surface of said skin tissue at least partially in response to said penetrating said skin tissue to said initial penetration depth, wherein said second angle is substantially equal to about an angle of hair growth; and penetrating said skin tissue to a selectable depth of between about 2.0 millimeters and about 7.0 millimeters while substantially maintaining said tubular punch at said second angle with respect to said surface of said skin tissue and while maintaining said hair follicle within an interior space of said tubular punch;

removing said hair follicle from said skin tissue; and treating an incision site with a topical steroid at least 2 days after incision.

18. A process according to claim 17 wherein said treating an incision site with an antibiotic ointment further comprises applying said antibiotic ointment or said topical steroid to said incision site at least around the time of said incision.

19. A process according to claim 17 wherein said causing said cylindrical cutting end to further penetrate said skin tissue of said subject to a selectable depth comprises turning an adjustment screw component of said tubular punch.

20. A method of follicular extraction to reduce scarring comprising:

treating an incision site with a surgical lubricant;

contacting a surface of skin tissue at a first angle with respect to said surface of said skin tissue using a tubular punch having a cylindrical cutting end;

making a first incision about a hair follicle into said surface of skin tissue using said tubular punch;

penetrating said skin tissue with the tubular punch to an initial penetration depth of between about 0.05 millimeters and about 0.3 millimeters;

angling said tubular punch to a second angle with respect to said surface of said skin tissue at least partially in response to said penetrating said skin tissue to said initial penetration depth, wherein said second angle is substantially equal to about an angle of hair growth; and penetrating said skin tissue to a selectable depth of between about 2.0 millimeters and about 7.0 millimeters while substantially maintaining said tubular punch at said second angle with respect to said surface of said skin tissue and while maintaining said hair follicle within an interior space of said tubular punch; and removing said hair follicle from said skin tissue; and treating an incision site with an antibiotic ointment or a topical steroid.

21. The method according to claim 20 further comprising applying surgical lubricant to said cutting end of said tubular punch.

22. A process according to claim 20 wherein said treating an incision site with an antibiotic ointment further comprises applying said antibiotic ointment or said topical steroid to said incision site at least around the time of said incision.

23. A process according to claim 20 wherein said treating an incision site with an antibiotic ointment further comprises applying an antibiotic ointment to said incision site at least 2 days after incision.

24. A process according to claim 20 wherein said causing said cylindrical cutting end to further penetrate said skin tissue of said subject to a selectable depth comprises turning an adjustment screw component of said tubular punch.

* * * * *